(12) United States Patent
Zhang et al.

(10) Patent No.: US 9,126,040 B2
(45) Date of Patent: *Sep. 8, 2015

(54) IMPLANTABLE ACOUSTIC SENSOR

(71) Applicants: Andy L. Zhang, East Melbourne (AU); Peter M. Seligman, Essendon (AU); Anthony Klein, Parkville (AU); Robert Cowan, Prahran (AU)

(72) Inventors: Andy L. Zhang, East Melbourne (AU); Peter M. Seligman, Essendon (AU); Anthony Klein, Parkville (AU); Robert Cowan, Prahran (AU)

(73) Assignee: Hearworks Pty, Limited, East Melbourne, Victoria (AU)

( * ) Notice: Subject to any disclaimer, the term of this patent is extended or adjusted under 35 U.S.C. 154(b) by 95 days.

This patent is subject to a terminal disclaimer.

(21) Appl. No.: 13/855,335

(22) Filed: Apr. 2, 2013

(65) Prior Publication Data

US 2013/0289654 A1    Oct. 31, 2013

Related U.S. Application Data

(63) Continuation of application No. 12/547,189, filed on Aug. 25, 2009, now Pat. No. 8,412,342, which is a continuation-in-part of application No. 10/986,812, filed on Nov. 15, 2004, now Pat. No. 7,580,754.

(30) Foreign Application Priority Data

Nov. 14, 2003   (AU) ................................ 2003906267

(51) Int. Cl.
| | |
|---|---|
| *A61N 1/36* | (2006.01) |
| *H01L 41/25* | (2013.01) |
| *H04R 9/08* | (2006.01) |

(52) U.S. Cl.
CPC ............ *A61N 1/36032* (2013.01); *H01L 41/25* (2013.01); *H04R 9/08* (2013.01); *H04R 2225/67* (2013.01); *Y10T 29/42* (2015.01)

(58) Field of Classification Search
USPC ..................... 607/1–2, 55–57, 115–116, 118, 607/136–137
See application file for complete search history.

(56) References Cited

U.S. PATENT DOCUMENTS

| | | |
|---|---|---|
| 5,061,282 A | 10/1991 | Jacobs |
| 5,772,575 A | 6/1998 | Lesinski et al. |
| 5,782,744 A | 7/1998 | Money |
| 6,259,951 B1 | 7/2001 | Kuzma et al. |

OTHER PUBLICATIONS

"Product Search—Piezoceramic Mics—BL series." Knowles Electronics. <http://www.knowles.com/search/search.do> (Feb. 25, 2008).

*Primary Examiner* — Deborah Malamud

(57) ABSTRACT

An implantable sound pickup system. The system comprises an intracochlear acoustic sensor implantable in a recipient's cochlea comprising: piezoelectric element configured to detect pressure waves in the perilymph of the cochlea when the acoustic sensor is at least partially implanted in the cochlea, and to produce electrical signals corresponding to the detected pressure waves.

20 Claims, 12 Drawing Sheets

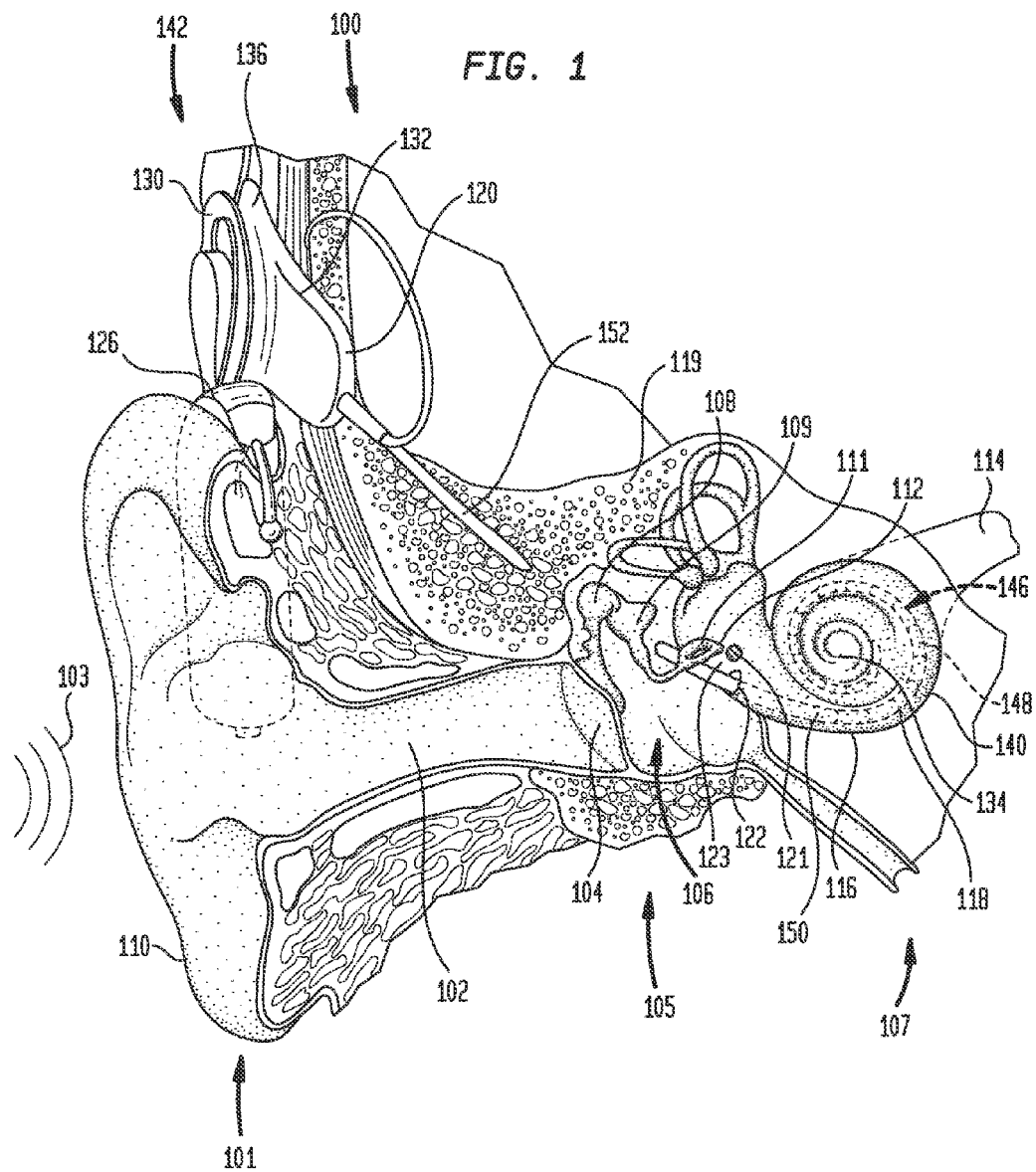

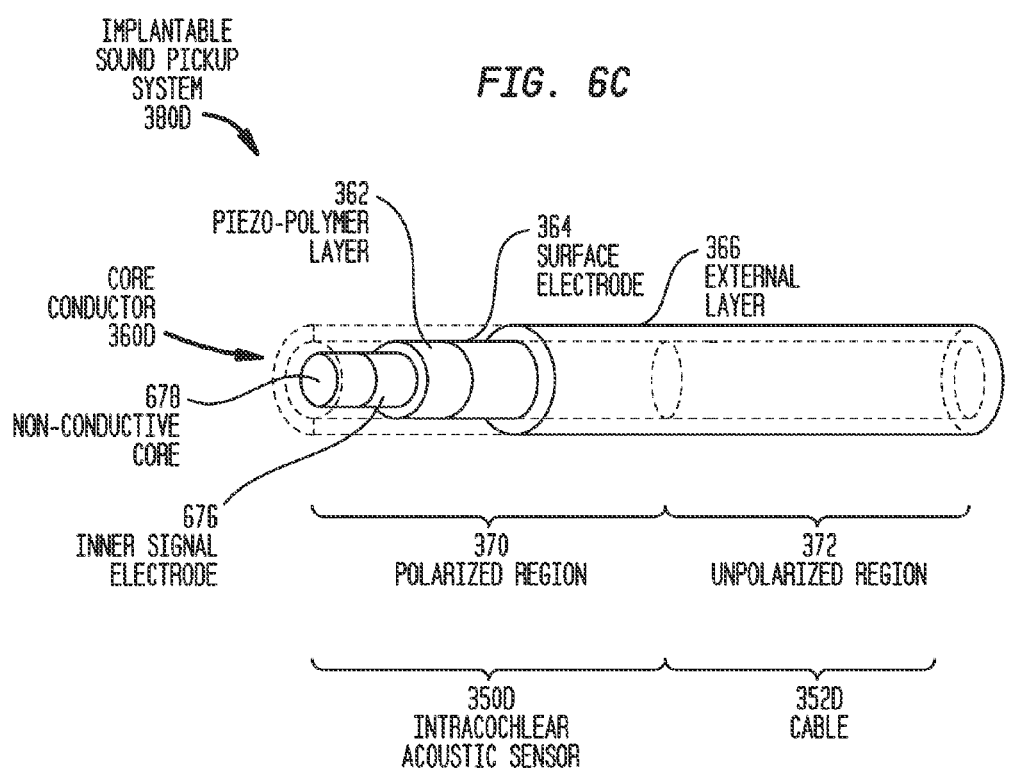

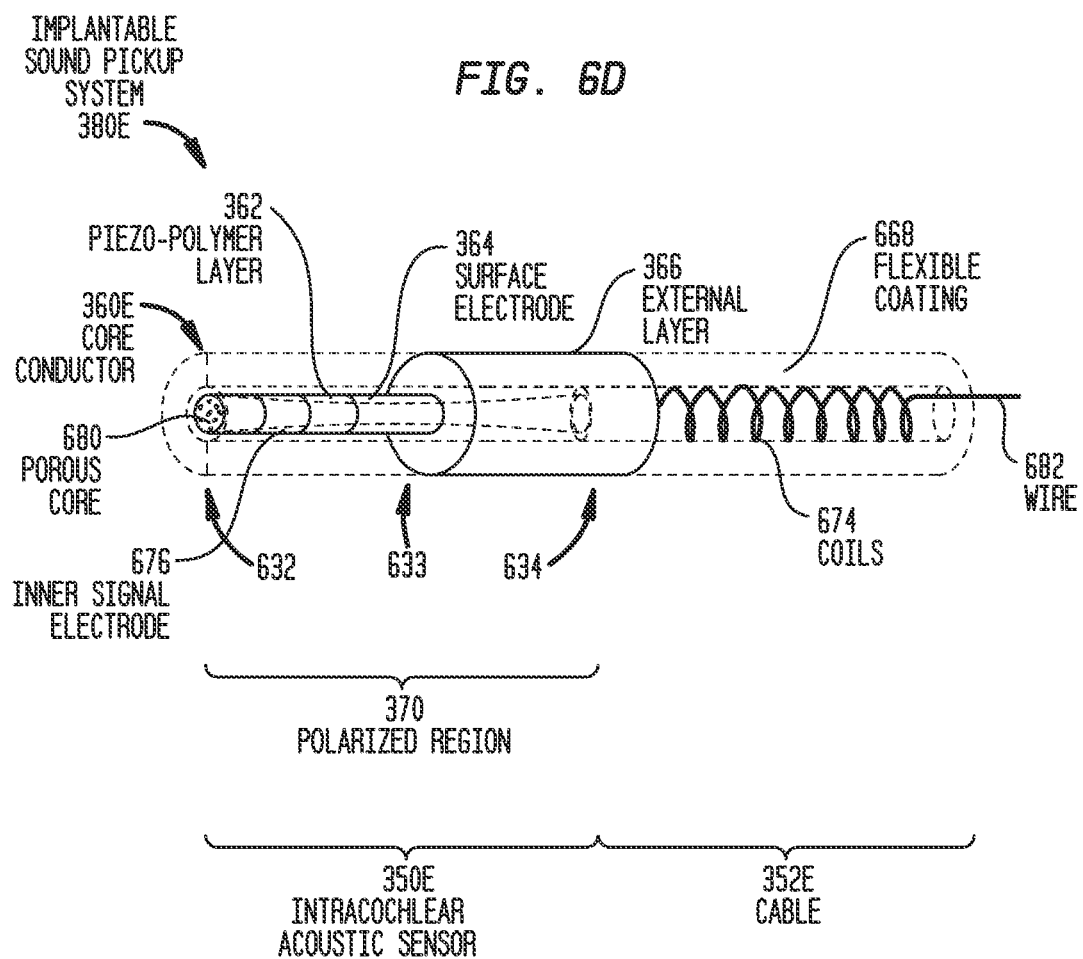

IMPLANTABLE ACOUSTIC SENSOR

CROSS-REFERENCE TO RELATED APPLICATIONS

The present application is a Continuation Application of U.S. patent application Ser. No. 12/547,189 filed Aug. 25, 2009, now U.S. Pat. No. 8,412,342, which is a continuation-in-part of U.S. patent application Ser. No. 10/986,812, filed Nov. 15, 2004, now U.S. Pat. No. 7,580,754, which claims priority from Australian Provisional Patent Application No. 2003906267, filed Nov. 14, 2003, which are hereby incorporated by reference herein.

BACKGROUND

1. Field of the Disclosure

The present disclosure relates generally to acoustic sensors, and more particularly, to an implantable acoustic sensor.

2. Related Art

Hearing loss, which may be due to many different causes, is generally of two types, conductive and sensorineural. In some cases, a person suffers from hearing loss of both types. Conductive hearing loss occurs when the normal mechanical pathways for sound to reach the cochlea are impeded, for example, by damage to the ossicles. Individuals who suffer from conductive hearing loss typically have some form of residual hearing because the hair cells in the cochlea are undamaged. As a result, individuals suffering from conductive hearing loss typically receive an implantable hearing prosthesis that generates mechanical motion of the cochlea fluid. Some such hearing prostheses, such as acoustic hearing aids, middle ear implants, etc., include one or more components implanted in the recipient, and are referred to herein as implantable hearing prostheses.

In many people who are profoundly deaf, however, the reason for their deafness is sensorineural hearing loss. Sensorineural hearing loss occurs when there is damage to the inner ear, or to the nerve pathways from the inner ear to the brain. As such, many individuals suffering from sensorineural hearing loss are thus unable to derive suitable benefit from hearing prostheses that generate mechanical motion of the cochlea fluid. As a result, implantable hearing prostheses that deliver electrical stimulation to nerve cells of the recipient's auditory system have been developed for persons whom do not derive adequate benefit from conventional hearing aids. Such electrically-stimulating hearing prostheses deliver electrical stimulation to nerve cells of the recipient's auditory system thereby providing the recipient with a hearing percept. Electrically-stimulating hearing prostheses include, for example, auditory brain stimulators and cochlear prostheses (commonly referred to as cochlear prosthetic devices, cochlear implants, cochlear devices, and the like; simply "cochlear implants" herein.)

Oftentimes sensorineural hearing loss is due to the absence or destruction of the cochlear hair cells which transduce acoustic signals into nerve impulses. It is for this purpose that cochlear implants have been developed. Cochlear implants provide a recipient with a hearing percept by delivering electrical stimulation signals directly to the auditory nerve cells, thereby bypassing absent or defective hair cells that normally transduce acoustic vibrations into neural activity. Such devices generally use an electrode array implanted in the cochlea so that the electrodes may differentially activate auditory neurons that normally encode differential pitches of sound.

Auditory brain stimulators are used to treat a smaller number of recipients with bilateral degeneration of the auditory nerve. For such recipients, the auditory brain stimulator provides stimulation of the cochlear nucleus in the brainstem.

Totally or fully implantable forms of the above and other implantable hearing prostheses have been developed to treat a recipient's conductive, sensorineural and/or combination hearing loss. As used herein, a totally implantable hearing prosthesis refers to an implantable prosthesis that is capable of operating, at least for a finite period of time, without an external device.

SUMMARY

In one aspect of the present disclosure, an implant is provided. The implant comprises: an intracochlear acoustic sensor implantable in a recipient's cochlea, the sensor comprising: a piezoelectric element configured to detect pressure waves in the perilymph of the cochlea when the acoustic sensor is at least partially implanted in the cochlea, and to produce electrical signals corresponding to the detected pressure waves.

In a still other aspect of the present disclosure, an implant is provided. The implant comprises: an intracochlear acoustic sensor implantable in a recipient's cochlea comprising: a piezoelectric element configured to detect pressure waves in the perilymph of the cochlea when the acoustic sensor is at least partially implanted in the cochlea, and to produce electrical signals corresponding to the detected pressure waves; and an electrode assembly configured to deliver electrical stimulation signals, generated based on at least the electrical signals produced by the piezoelectric element, to the recipient's cochlea.

In another aspect of the present disclosure, a method of manufacturing an intracochlear implant is provided: The method comprises: coating an elongate core conductor with a piezoelectric element; polarizing a region of the piezoelectric element; coating the piezoelectric element with a surface electrode layer; and coating the surface electrode layer with an external passivation layer.

In another aspect of the present disclosure, a method of manufacturing an intracochlear implant is provided. The method comprises: an intracochlear acoustic sensor implantable in a recipient's cochlea, the sensor comprising a piezoelectric element configured to detect pressure waves in a fluid of the cochlea when the acoustic sensor is at least partially implanted in the cochlea, and to produce electrical signals corresponding to the detected pressure waves.

BRIEF DESCRIPTION OF THE DRAWINGS

Embodiments of the present disclosure are described below with reference to the attached drawings, in which:

FIG. 1 is a perspective view of an exemplary totally implantable cochlear implant, in which embodiments of the present disclosure may be implemented;

FIG. 6C is a side view of a sound pickup system in accordance with embodiments of the present disclosure, from which sections have been removed;

FIG. 6D is a side view of a sound pickup system in accordance with embodiments of the present disclosure, from which sections have been removed;

DETAILED DESCRIPTION

Figure 2A:
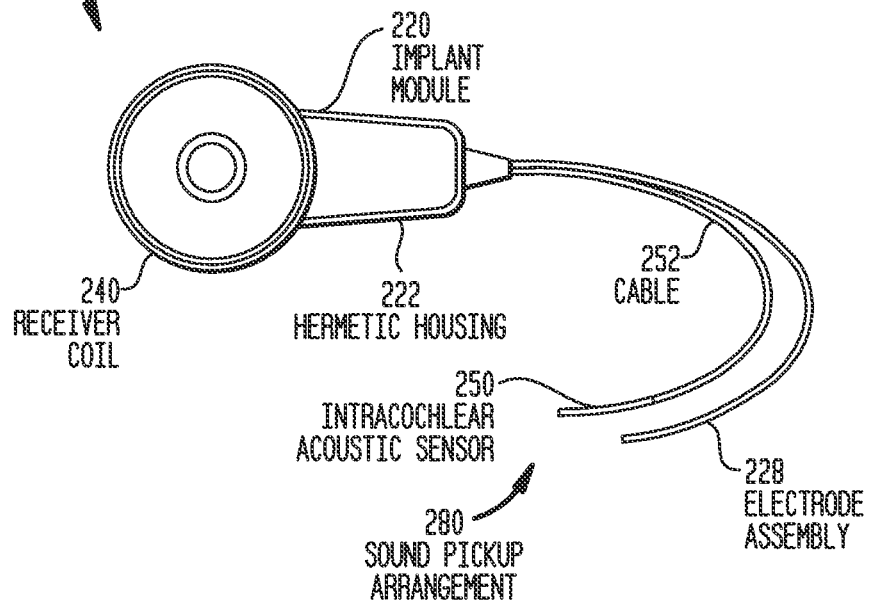
FIG. 2A is a side view of a totally implantable cochlear implant in accordance with embodiments of the present disclosure.

Aspects of the present disclosure are generally directed to an implantable sound pickup system for a hearing prosthesis. The implantable sound pickup system includes an intracochlear acoustic sensor implantable in a recipient's cochlea, and a cable connecting the sensor to one or more other components of the hearing prosthesis. The intracochlear acoustic sensor comprises a core conductor, and a piezoelectric element disposed on the surface of the core conductor. The piezoelectric element is configured to detect pressure waves in the cochlea fluid when the core conductor is at least partially implanted in the cochlea, and to produce electrical signals corresponding to the detected pressure waves.

In certain embodiments, the sound pickup system is a component of a totally or fully implantable cochlear prosthesis (commonly referred to as a cochlear prosthetic device, cochlear implant, cochlear device, and the like; simply "cochlear implants" herein). As noted, the intracochlear acoustic sensor detects an acoustic sound signal through movement of the cochlea fluid, and generates corresponding electrical signals. The cochlear implant further comprises an electrode assembly that delivers to the recipient's cochlea electrical stimulation signals generated based on the acoustic signals detected by the sensor.

Embodiments of the present disclosure will be primarily described with reference to the use of the sound pickup system in a cochlear implant. It would be appreciated that the sound pickup system may also be implemented any partially or fully implantable hearing prosthesis now known or later developed, including, but not limited to, acoustic hearing aids, auditory brain stimulators, middle ear mechanical stimulators, hybrid electro-acoustic prosthesis or other prosthesis that electrically, acoustically and/or mechanically stimulate components of the recipient's outer, middle or inner ear.

FIG. 1 is perspective view of a totally implantable cochlear implant, referred to as cochlear implant 100, implanted in a recipient. The recipient has an outer ear 101, a middle ear 105 and an inner ear 107. Components of outer ear 101, middle ear 105 and inner ear 107 are described below, followed by a description of cochlear implant 100.

In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown, cochlear implant 100 comprises one or more components which are temporarily or permanently implanted in the recipient. Cochlear implant 100 is shown in FIG. 1 with an external device 142 which is configured to provide power to the cochlear implant.

In the illustrative arrangement of FIG. 1, external device 142 comprises a power source (not shown) disposed in a Behind-The-Ear (BTE) unit 126. External device 142 also includes components of a transcutaneous energy transfer link, collectively referred to as an external energy transfer assembly. The transcutaneous energy transfer link is used to transfer power and/or data to cochlear implant 100. As would be appreciated, various types of energy transfer, such as infrared (IR), electromagnetic, capacitive and inductive transfer, may be used to transfer the power and/or data from external device 142 to cochlear implant 100. In the illustrative embodiments of FIG. 1, the external energy transfer assembly comprises an external coil 130 that forms part of an inductive radio frequency (RF) communication link. External coil 130 is a wire antenna coil comprised of multiple turns of electrically insulated single-strand or multi-strand platinum or gold wire. External device 142 also includes a magnet (not shown) positioned within the turns of wire of external coil 130. It should be appreciated that the external device shown in FIG. 1 is merely illustrative, and other external devices may be used with embodiments of the present disclosure.

Cochlear implant 100 comprises an internal energy transfer assembly 132 which may be positioned in a recess of the temporal bone adjacent auricle 110 of the recipient. Internal energy transfer assembly 132 is a component of the transcutaneous energy transfer link and receives power and/or data from external device 142. In the illustrative embodiment, the energy transfer link comprises an inductive RF link, and internal energy transfer assembly 132 comprises a primary internal coil 136. Internal coil 136 is typically a wire antenna coil comprised of multiple turns of electrically insulated single-strand or multi-strand platinum or gold wire.

Cochlear implant 100 comprises a main implant module 120. In embodiments of the present disclosure, internal energy transfer assembly 132 and implant module 120 are hermetically sealed within a biocompatible housing.

Cochlear implant 100 further comprises an intracochlear acoustic sensor 150 connected to implant module 120 via a cable 152. As shown, cable 152 has a proximal end connected to implant module 120, and a distal end connector to intracochlear acoustic sensor 150 positioned in cochlea 140. Cable 152 extends from implant module 120 to intracochlear acoustic sensor 150 through mastoid bone 119. As described below, cable 152 and intracochlear acoustic sensor 150 are collectively referred to as a sound pickup system.

In the embodiments of FIG. 1, intracochlear acoustic sensor 150 is disposed in basal region 116 of cochlea 140. An electrode assembly 118 extends from the distal end of intracochlear acoustic sensor 150 towards the apical end of cochlea 140, referred to as cochlea apex 134. Electrode assembly 118 comprises a longitudinally aligned and distally extending array 146 of electrodes 148, sometimes referred to as electrode array 146 herein, disposed along a length thereof. Although electrode array 146 may be disposed on electrode assembly 118, in most practical applications, electrode array 146 is integrated into electrode assembly 118. As such, electrode array 146 is referred to herein as being disposed in electrode assembly 118.

In the embodiments of FIG. 1, electrode assembly 118 and the sound pickup system are integrated with one another and form a single implantable component. As described in greater detail below, in alternative embodiments of the present disclosure the sound pickup system and electrode assembly 118 comprise physically separate and independent components.

Intracochlear acoustic sensor 150 and electrode assembly 118 may be inserted into cochlea 140 via a cochleostomy 122. In other circumstances, a cochleostomy may be formed through round window 121, oval window 112, the promontory 123, etc.

As described in detail below, intracochlear acoustic sensor 150 is configured to receive sounds by detecting pressure waves in the recipient's inner ear fluid, such as the perilymph. More specifically, an acoustic pressure or sound wave 103 is collected by auricle 110 and channeled through ear canal 102, resulting in the vibration of tympanic membrane 104. The vibration of tympanic membrane 104 is coupled to oval window 112 through bones 108, 109 and 111 of middle ear 105, causing oval window 112 to vibrate. This vibration sets up waves of fluid motion of the perilymph, referred to herein as pressure waves, within cochlea 140 that are detected by intracochlear acoustic sensor 150. As described below, intracochlear acoustic sensor 150 produces electrical signals corresponding to the detected pressure waves, and relays the electrical signals to implant module 120 via cable 152. In certain embodiments, the electrical signals provided to implant module 120 are current signals that are converted to voltage signals by a charge amplifier (not shown). These voltage signals are provided to a processing module (also not shown) in implant module 120 that generates data signals corresponding to the received sound. The data signals are provided to a stimulator unit (also not shown) which generates electrical stimulation signals based on the data signals. The electrical stimulation signals are delivered to the recipient via electrode assembly 118, thereby evoking perception of the received sound signals by the recipient.

As noted, cochlear implant 100 comprises a totally implantable prosthesis that is capable of operating, at least for a period of time, without the need for external device 142. Therefore, cochlear implant 100 further comprises a rechargeable power source (not shown) that stores power received from external device 142. The power source may comprise, for example, a rechargeable battery. During operation of cochlear implant 100, the power stored by the power source is distributed to the various other implanted components as needed. The power source may be located in implant module 120, or disposed in a separate implanted location.

Figure 2B:
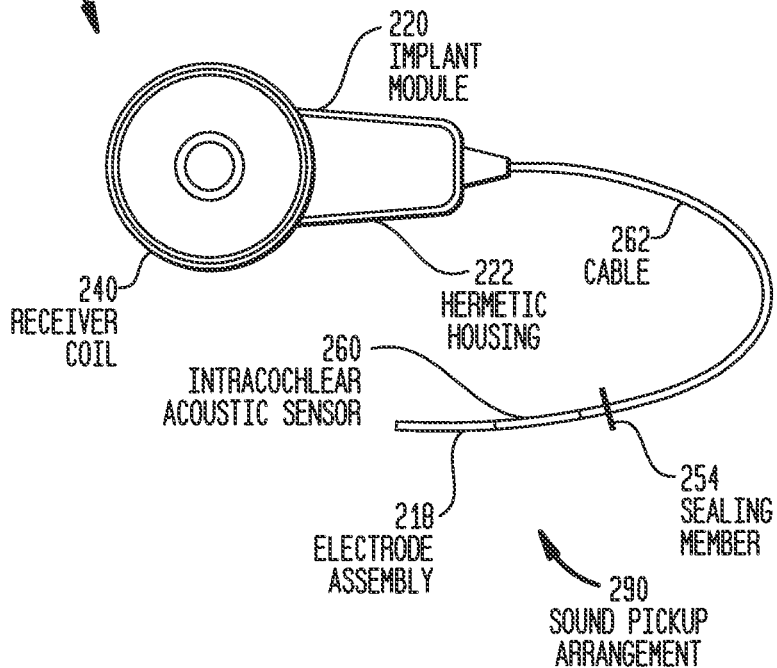
FIG. 2B is a side view of a totally implantable cochlear implant in accordance with embodiments of the present disclosure.

FIGS. 2A and 2B are side views of embodiments of cochlear implant 100 of FIG. 1, referred to as cochlear implants 200A and 200B, respectively. Cochlear implants 200A and 200B each comprise an implant module 220 that is substantially similar to implant module 120 described above with reference to FIG. 1. Specifically, implant modules 220 comprise various electronic components (i.e. processing module, stimulator unit, etc.) hermetically sealed in a housing 222 with components of an internal energy transfer assembly 132 (FIG. 1). For ease of illustration, only receiver coil 240 of internal energy transfer assembly 132 is shown in FIGS. 2A and 2B.

Cochlear implant 200A of FIG. 2A has an elongate electrode assembly 228 extending from implant module 220. Similar to electrode assembly 118 of FIG. 1, electrode assembly 228 comprises a longitudinally aligned and distally extending array of electrodes. Electrode assembly 228 has a proximal end connected to implant module 220, and a distal end configured to be implanted in a recipient's cochlea. In some embodiments electrode assembly 228 may be implanted at least in a recipient's basal region, and sometimes further. For example, electrode assembly 228 may extend towards the apical end of the recipient's cochlea. In certain circumstances, electrode assembly 228 may be inserted into the cochlea via a cochleostomy formed through the round window, oval window, the promontory 123, etc. It would be appreciated that electrode assembly 228 is inserted into the cochlea so as have minimal impact on the flow of the cochlea fluid. That is, the electrode assembly 228 is implanted so as not to disturb, or to have minimal effect on, cochlea hydrodynamics.

Cochlear implant 200A further includes a sound pickup system 280 comprising an intracochlear acoustic sensor 250 for detecting sound, and a cable 252 connecting the sensor to implant module 220. As explained above, an acoustic pressure or sound wave is collected by the recipient's auricle and channeled through the ear canal, causing vibration of the tympanic membrane. This vibration is transferred from the tympanic membrane to the recipient's oval window through the bones of the middle ear, causing the oval window to vibrate. The vibration of the oval window sets up pressures waves within the cochlea perilymph that are detected by intracochlear acoustic sensor 250. As described in greater detail below, intracochlear acoustic sensor 250 produces electrical signals corresponding to the detected pressure waves. These electrical signals are relayed to implant module 120 via cable 252. Similar to electrode assembly 228, intracochlear acoustic sensor 250 is implanted so as not to disturb, or to have minimal effect on, cochlea hydrodynamics.

In the embodiments of FIG. 2A, electrode assembly 228 and intracochlear sensor 250 are physically separate components that may be independently implanted in a recipient's cochlea. FIG. 2B illustrates embodiments in which a sound pickup system 290 and an electrode assembly 218 comprise a unitary, integrated component. More specifically, in the embodiments of FIG. 2B intracochlear acoustic sensor 260 is configured to be implanted in the basal region of a recipient's cochlea, and electrode assembly 218 extends from the distal end of the sensor. In such embodiments, the electrical connections between the electrodes (not shown) of electrode assembly 218 and implant module 220 may extend through or around intracochlear acoustic sensor 260 through cable 262. Because sound pickup system 290 and electrode assembly 218 comprise an integrated component, only one cochlea insertion procedure is required during surgery. Similar to the embodiments of FIG. 2A, sound pickup system 290 and electrode assembly 218 are inserted into the cochlea so as not to disturb, or to have minimal effect on, cochlea hydrodynamics.

As described above, intracochlear acoustic sensor 260 senses sound by detecting pressures waves within the cochlea perilymph. Intracochlear acoustic sensor 260 produces electrical signals corresponding to the detected pressure waves, and relays the electrical signals to implant module 220 via cable 262.

The embodiments of FIG. 2B further illustrate the use of a sealing member 254 disposed about cable 262. Sealing member 262 is configured to be positioned outside the cochlea and is operatively in contact with the external wall of the cochlea to seal perilymph inside the cochlea. In certain embodiments, sealing member 254 is made from a biocompatible material such as titanium. It would be appreciated that electrode assembly 218 and intracochlear acoustic sensor 260 may, in certain circumstances, be implanted in a recipient so as to seal the cochlea without the need for sealing member 254. It would also be appreciated that similar sealing members may used in the embodiments of FIG. 2A to seal the openings in the cochlea through which cable 252 and electrode assembly 228 extend.

Figure 3:
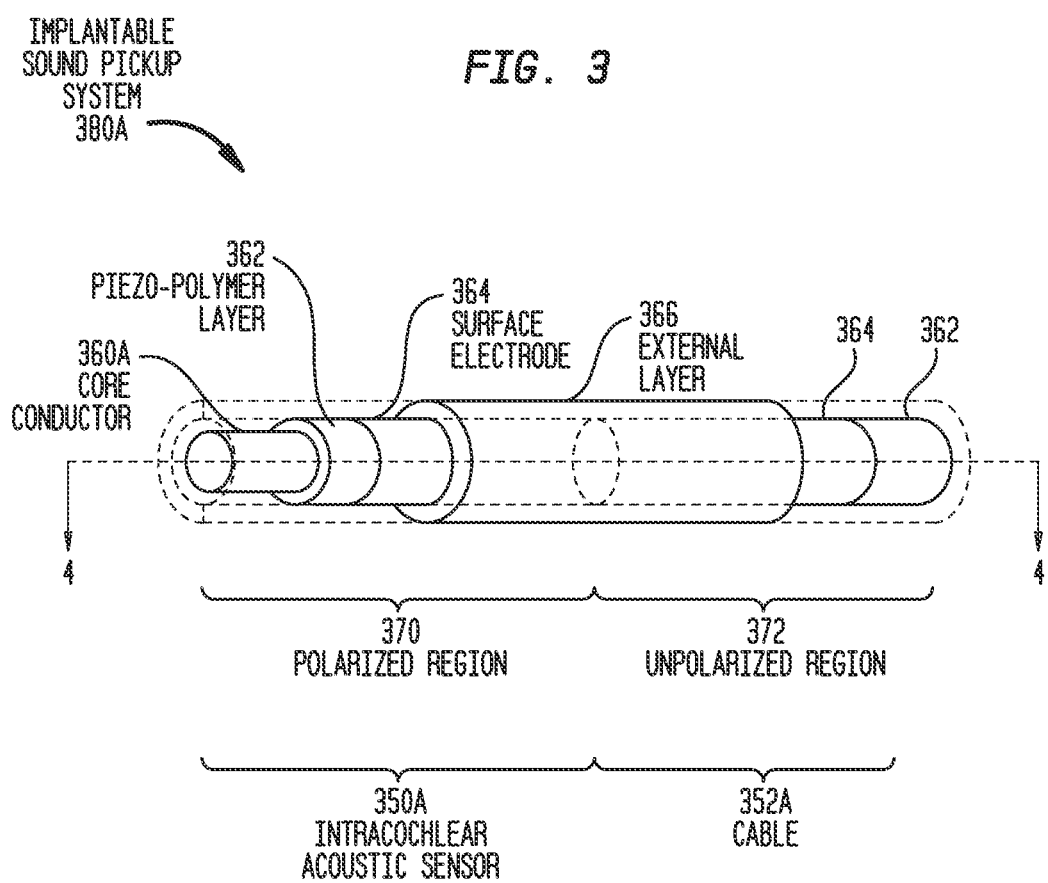
FIG. 3 is a side view of a sound pickup system in accordance with embodiments of the present disclosure, from which sections have been removed.

FIG. 3 is a side view of one embodiment of a sound pickup system 380A in accordance with aspects of the present disclosure. As described below, sections of sound pickup system 380A are removed to illustrate all elements of the system.

In the illustrative embodiments of FIG. 3, sound pickup system 380A comprises an intracochlear acoustic sensor 350A, and a cable 352A formed into a integrated component. Sound pickup system 380A includes an elongate core conductor 360A extends through both of sensor 350A and cable 352A. Core conductor 360A comprises an elongate metallic element, such as, for example, platinum, titanium, or other type of conductive wire. Disposed on the surface of core conductor 360A is a piezo-polymer layer 362. Piezo-polymer layer 362 is formed from a material that, when polarized, displays the piezoelectric effect. That is, the polarized region of piezo-polymer layer 362 produces an electrical signal upon the imposition of a mechanical stress or strain to the layer. As described below, pressure waves within a recipient's cochlea cause a mechanical stress on piezo-polymer layer 362. The mechanical stress causes the polarized region of piezo-polymer layer 362 to generate electrical signal corresponding to the detected pressure waves.

As used herein, piezoelectric materials usable in embodiments of the present disclosure include piezo-polymers, piezoceramics and any other suitable material that may be polarized to exhibit the piezoelectric effect. For example, in certain embodiments of the present disclosure piezoelectric element 362 comprises a piezo-polymer layer 362 such as polyvinylidene fluoride (PVDF) or a PVDF copolymer such as P(VDF-TrFE).

As shown, in the embodiments of FIG. 3 piezo-polymer layer 362 is a unitary layer disposed circumferentially about the length of core conductor 360A. In alternative embodiments piezo-polymer layer 362 comprises a piezoelectric tape spirally wrapped around core conductor 360A.

Also as shown in FIG. 3, a surface electrode 364 is disposed on piezo-polymer layer 362. Surface electrode 364 is a thin metallic element that functions as a ground electrode and as an electromagnetic interference (EMI) shield. Surface electrode 364 may be a thin film layer formed from any suitable biocompatible conductive material such as, for example, titanium, platinum, gold, or other material. A thin external passivation layer 366 is disposed on the outer surface of surface electrode 364 to electrically isolate surface electrode 364 from the surrounding cochlea fluid. External layer 366 may be formed from any suitable biocompatible insulative material such as parylene or silicon rubber.

In embodiments of FIG. 3A, piezo-polymer layer 362, surface electrode 364 and external layer 366 each circumferentially surround core conductor 360A, or the previously applied layer, and substantially extend the length of core conductor 360A. As shown in FIGS. 4A-4E, a proximal end of core conductor 360A remains exposed to permit sound pickup system 380A to be connected to an additional component, such as an implant module.

As noted above, a selected section of piezo-polymer layer 362 is polarized. In the embodiments of FIG. 3A, the distal region of piezo-polymer layer 362 is polarized, and is referred to as polarized region 370. The remainder of piezo-polymer layer 362 remains unpolarized and is referred to as unpolarized region 372. When implanted in a recipient's cochlea, polarized region 370 detects pressure waves in the cochlea fluid, and generates electrical signals representative of the pressure waves. These electrical signals are relayed through core conductor 360A to the implant module. The section of sound pickup system 380A containing polarized region 370 is referred to herein as intracochlear acoustic sensor 350A, while the remainder of sound pickup system 380A is referred to as cable 352A.

As noted, the electrical signals generated by polarized region 370 of piezo-polymer layer 362 are relayed to implant module via core conductor 360A. In certain embodiments, the relayed electrical signals are current signals that are converted to voltage signals by a charge amplifier (not shown) in the implant module. An exemplary charge amplifier is described below with reference to FIG. 8.

In specific embodiments of the present disclosure, only intracochlear acoustic sensor 350A is implanted in the recipient's cochlea. In alternative embodiments, a portion of cable 352A is also implanted in the cochlea. In further embodiments, only a portion of intracochlear acoustic sensor 350A is implanted in the cochlea.

As would be appreciated, intracochlear acoustic sensor 350A is implanted through a natural or artificial opening in the recipient's cochlea. Intracochlear acoustic sensor 350A is also implanted so as to have minimal impact on the cochlear fluid dynamics. In certain embodiments, the natural or artificial opening through which sensor 350A is inserted should be sealed so as to reduce the impact on the fluid flow. Therefore, as noted above with reference to FIGS. 2A and 2B, in certain embodiments intracochlear sensor 350A and/or cable 352A may be configured to seal the opening through which sensor 350A is inserted. In alternative embodiments, a sealing member may be positioned on the surface of intracochlear sensor 350A or on the surface of cable 352A to seal the opening.

Figure 4A:
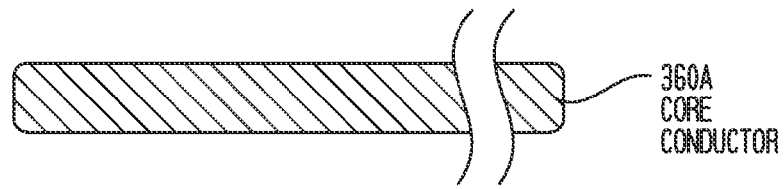
FIG. 4A is a cross-sectional view of the sound pickup system of FIG. 3 taken along line 4-4, during a stage of the manufacturing process.
Figure 4B:
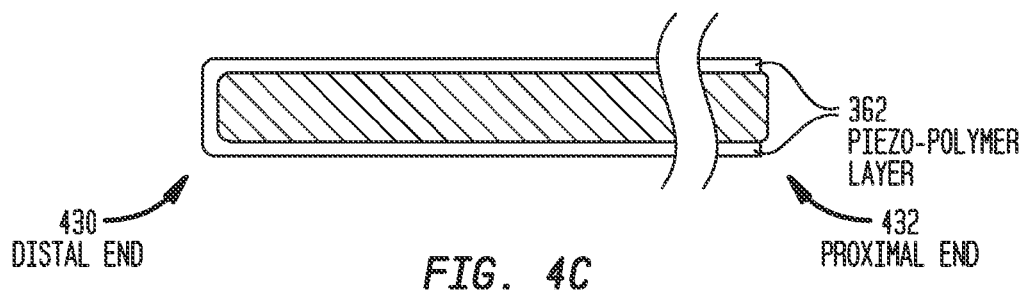
FIG. 4B is a cross-sectional view of the sound pickup system of FIG. 3 taken along line 4-4, during a stage of the manufacturing process.
Figure 4C:
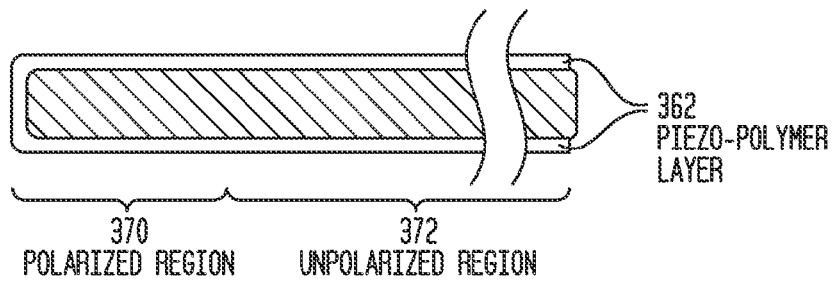
FIG. 4C is a cross-sectional view of the sound pickup system of FIG. 3 taken along line 4-4, during a stage of the manufacturing process.
Figure 4D:
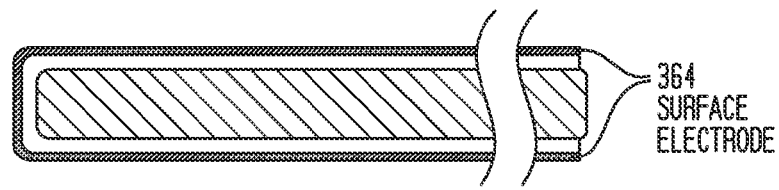
FIG. 4D is a cross-sectional view of the sound pickup system of FIG. 3 taken along line 4-4, during a stage of the manufacturing process.
Figure 4E:
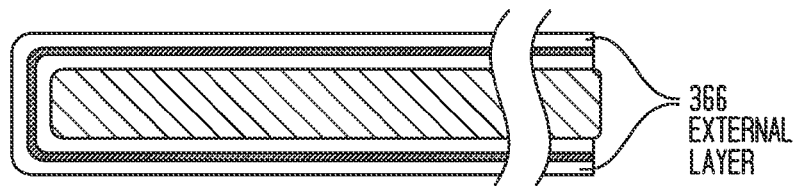
FIG. 4E is a cross-sectional view of the sound pickup system of FIG. 3 taken along line 4-4, during a stage of the manufacturing process.
Figure 5:
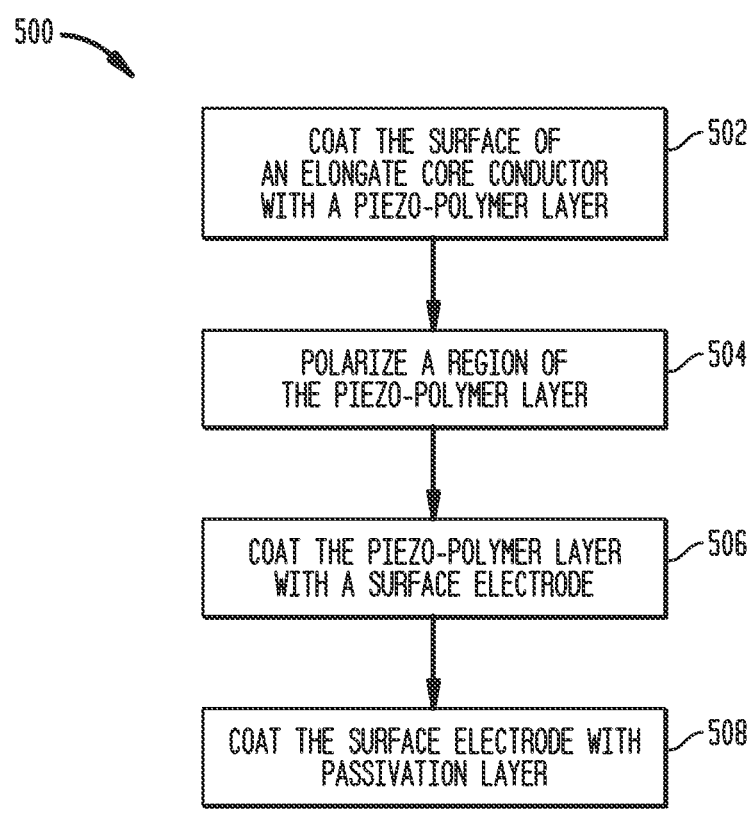
FIG. 5 is a flowchart illustrating the steps performed during manufacture of the sound pickup system of FIG. 3.

FIGS. 4A-4E are cross-sectionals views of sound pickup system 380A of FIG. 3 during various stages of the manufacturing process. The views of FIGS. 4A-4E are taken along cross-sectional line 4-4 of FIG. 3. Similarly, FIG. 5 is a flowchart illustrating a manufacturing process 500 used to form sound pickup system 380A. For ease of illustration, manufacturing process 500 of FIG. 5 will be described with reference to FIGS. 4A-4E.

In embodiments of the present disclosure, a core conductor 360A is first provided. FIG. 4A is a cross-sectional view of an exemplary core conductor 360 formed from a platinum wire. In specific embodiments of the present disclosure, the platinum core conductor 360A has a circular cross-section. It would be appreciated that a core conductor having other cross-sectional shapes and different dimensions may also be used.

At block 502, the surface of a portion of core conductor 360A is coated with piezo-polymer layer 362. As shown in FIG. 4B, piezo-polymer layer 362 circumferentially extends around the surface of core conductor 360A. Also as shown in FIG. 4B, piezo-polymer layer 362 is disposed on core conductor 360A such that distal end 430 is fully coated, but that proximal end 432 remains uncoated.

At block 504, a region of piezo-polymer layer is polarized using, for example, corona or plasma polarization methods. In the specific embodiments of FIG. 4C, the distal region of the piezo-polymer layer 362 is polarized to form polarized region 370. The remainder of piezo-polymer layer 362 remains unpolarized and is referred to as unpolarized region 372. For ease of illustration polarized region 370 and unpolarized region 372 are not differentiated in FIGS. 4D and 4E.

At block 506, the surface of piezo-polymer layer 362 is coated with an electrode layer, referred to as surface electrode 364. As shown in FIG. 4D, surface electrode 364 extends circumferentially about piezo-polymer layer 362, and covers the distal end thereof. However, as noted above the proximal end 432 of core conductor 360A remains exposed. In the specific embodiments illustrated in FIG. 4D, surface electrode 364 comprises a metallic thin film layer made from gold, platinum or other material. Surface electrode 364 is sputtered onto the surface of the piezo-polymer layer 362. It would be appreciated that this step can be performed prior to, or after, connection of core conductor 360A to an implant module.

At block 508, the surface of surface electrode 364 is coated with an external passivation layer 366. As shown in FIG. 4E, external layer 366 extends circumferentially about surface electrode 364, and covers the distal end thereof. However, as noted above the proximal end 432 of core conductor 360A remains exposed. In the embodiments of FIG. 4E, external layer 366 comprises a thin layer of parylene that substantially free from holes, and which conforms to the outer surface of surface electrode 364.

Figure 6A:
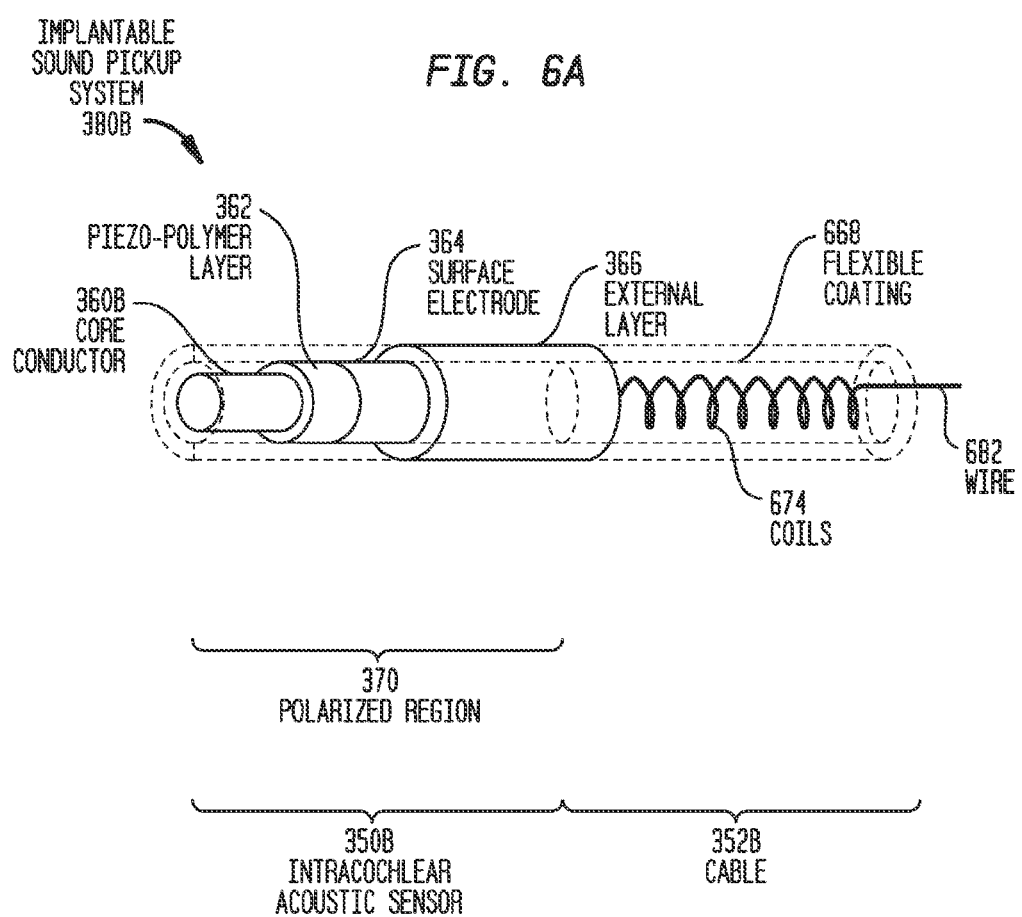
FIG. 6A is a side view of a sound pickup system in accordance with embodiments of the present disclosure, from which sections have been removed.

It would be appreciated that the embodiments of FIGS. 4A-4E are merely illustrative and are not shown to scale. It would also be appreciated that the thickness of the various layers of FIGS. 4A-4E, or the relative thickness of layers to one another is not indicative of the thickness utilized in embodiments of the present disclosure FIG. 6A is a partial cross-sectional view of one embodiment of a sound pickup system 380B in accordance with aspects of the present disclosure. As shown, sound pickup system 380B comprises an intracochlear acoustic sensor 350B, and a cable 352B. An elongate core conductor 360B that is substantially the same as core conductor 360A of FIG. 3 extends through acoustic sensor 350B. However, unlike core conductor 360A of FIG. 3, core conductor 360B does not extend through cable 352B.

In the embodiments of FIG. 6A, core conductor 360B is coated with a piezo-polymer layer 362. Although FIG. 6A illustrates the use of piezo-polymer 362, it would be appreciated that other piezoelectric elements may also be used in alternative embodiments. Intracochlear acoustic sensor 350B also comprises a surface electrode 364 disposed on the surface of piezo-polymer layer 362, and a thin external passivation layer 366 disposed on the surface of surface electrode 364. Surface electrode 364 and external layer 366 are again implemented as described above with reference to FIG. 3.

As shown in FIG. 6A, piezo-polymer layer 362, surface electrode 364 and external layer 366 each circumferentially surround core conductor 360B, or the previously applied layer, and extend at least the length of core conductor 360B. However, as noted above, core conductor 360B does not extend through cable 352B. Rather, a wire 682 is connected to the proximal end of core conductor 360B. Wire 682 is embedded in a flexible coating 668 such as a flexible silicone rubber. Flexible coating 668 extends from the proximal end of piezo-polymer layer 362 to adjacent the proximal end of wire 682. The proximal end of wire 682 remains exposed for electrical connection with an implant module.

In the embodiments of FIG. 6A, flexible coating 668 is disposed about wire 682 so that the outer dimensions of flexible coating 668 are substantially the same as the outer dimensions of piezo-polymer layer 362, and surface electrode 364 is disposed on the outer surface thereof. Similarly, external layer 366 is disposed on the outer surface of surface electrode 364.

As shown in FIG. 6A, all of piezo-polymer layer 362 is polarized so as to generate electrical signals representative of detected pressure waves. These electrical signals are relayed through core conductor 360B to wire 682 where they are provided to the implant module. The section of sound pickup system 380B containing polarized piezo-polymer layer 362 is referred to herein as intracochlear acoustic sensor 350B, while the remainder of sound pickup system 380B is referred to as cable 352B.

As noted above, cable 352B comprises wire 682 embedded in flexible coating 668. As shown, a section of wire 682 is formed into a helical shape and comprises a plurality of coils 674. Coils 674 provide strain relief to sound pickup system 380B. Specifically, coils 674 are embedded in flexible coating 668 to provide elongation of wire 682 if cable 352B is bent or otherwise subjected to external forces. This strain relief reduces the risk of the breakage of the electrical connection between an implant module and intracochlear sensor 350B in response to such flexing/bending of cable 352B.

As noted, the electrical signals generated by polarized piezo-polymer layer 362 are relayed to implant module via core conductor 360B and wire 682. In certain embodiments, the relayed electrical signals are current signals that are converted to voltage signals by a charge amplifier (not shown) in the implant module. An exemplary charge amplifier is described below with reference to FIG. 8.

In specific embodiments of the present disclosure, only intracochlear acoustic sensor 350B is implanted in the recipient's cochlea. In alternative embodiments, a portion of cable 352B is also implanted in the cochlea. In still other embodiments, only a portion of acoustic sensor 350B is implanted in the cochlea.

As would be appreciated, intracochlear acoustic sensor 350B is implanted through a natural or artificial opening in the recipient's cochlea. Intracochlear acoustic sensor 350B is also implanted so as to have minimal impact on the cochlear fluid dynamics. In certain embodiments, the natural or artificial opening through which sensor 350B is inserted should be sealed so as to reduce the impact on the fluid flow. Therefore, as noted above with reference to FIGS. 2A and 2B, in certain embodiments intracochlear sensor 350B and/or cable 352B may be configured to seal the opening through which sensor 350B is inserted. In alternative embodiments, a sealing member may be positioned on the surface of intracochlear sensor 350B or on the surface of cable 352B to seal the opening.

Figure 6B:
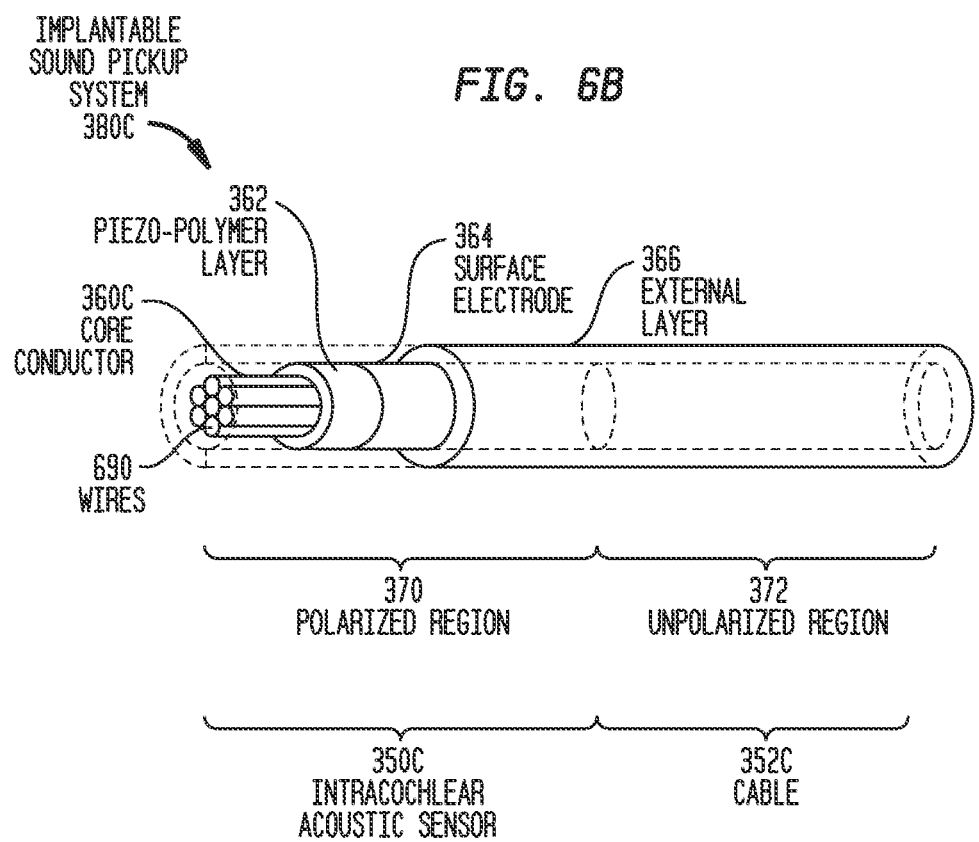
FIG. 6B is a side view of a sound pickup system in accordance with embodiments of the present disclosure, from which sections have been removed.

FIG. 6B is a partial cross-sectional view of another embodiment of a sound pickup system 380C in accordance with aspects of the present disclosure. As shown, sound pickup system 380C comprises intracochlear acoustic sensor 350C, and cable 352C. Sound pickup system 380C further comprises an elongate core conductor 360C that extends through both sensor 350C and cable 352C. In the embodiments of FIG. 6B, core conductor 360C comprises a bundle of, for example, a platinum, titanium, gold or other type of conductive wires 690. Wires 690 may each comprise single or multi-strand wires.

Similar to the embodiments of FIG. 3, core conductor 360C is coated with a piezo-polymer layer 362. Sound pickup system 380C also comprises a surface electrode 364 disposed on the surface of piezo-polymer layer 362, and a thin external passivation layer 366 disposed on the outer surface of surface electrode 364. Surface electrode 364 and external layer 366 are again implemented as described above with reference to FIG. 3.

As shown in FIG. 6A, piezo-polymer layer 362, surface electrode 364 and external layer 366 each circumferentially surround core conductor 360B, or the previously applied layer, and extend the length of core conductor 360C. Similar to the embodiments described above with reference to FIGS. 4A-4E, a proximal end of core conductor 360C remains exposed to permit sound pickup system 380C to be connected to an additional component, such as an implant module.

As described above, a selected section of piezo-polymer layer 362 is polarized. In the embodiments of FIG. 3A, the distal region of piezo-polymer layer 362 is polarized and is referred to as polarized region 370. The remainder of piezo-polymer layer 362 remains unpolarized and is referred to as unpolarized region 372. When implanted in a recipient's cochlea, polarized region 370 detects pressure waves in the cochlea fluid, and generates electrical signals representative of the pressure waves. These electrical signals are relayed through core conductor 360C to the implant module. The section of sound pickup system 380C containing polarized region 370 is referred to herein as intracochlear acoustic sensor 350C, while the remainder of sound pickup system 380C is referred to as cable 352C.

As noted, the electrical signals generated by polarized region 370 of piezo-polymer layer 362 are relayed to implant module via core conductor 360C. In certain embodiments, the relayed electrical signals are current signals that are converted to voltage signals by a charge amplifier (not shown) in the implant module. An exemplary charge amplifier is described below with reference to FIG. 8.

As would be appreciated, intracochlear acoustic sensor 350C is implanted through a natural or artificial opening in the recipient's cochlea. Intracochlear acoustic sensor 350C is also implanted so as to have minimal impact on the cochlear fluid dynamics. In certain embodiments, the natural or artificial opening through which sensor 350C is inserted should be sealed so as to reduce the impact on the fluid flow. Therefore, as noted above with reference to FIGS. 2A and 2B, in certain embodiments intracochlear sensor 350C and/or cable 352C may be configured to seal the opening through which sensor 350C is inserted. In alternative embodiments, a sealing member may be positioned on the surface of intracochlear sensor 350C or on the surface of cable 352C to seal the opening.

FIG. 6C is a partial cross-sectional view of a still other embodiment of a sound pickup system 380D in accordance with aspects of the present disclosure. As shown, sound pickup system 380D comprises intracochlear acoustic sensor 350D, and cable 352D. Sound pickup system 380D includes an elongate core conductor 360D that extends the through sensor 350D and cable 352D. In the embodiments of FIG. 6C, core conductor 360D comprises a non-conductive core 678 having a thin metallic film 676 disposed on the surface thereof. Metallic film 676 is sometimes referred to herein as inner signal electrode 676. Non-conductive core 678 may comprise a flexible polymer material, while inner signal electrode 676 comprises a layer of, for example, platinum, titanium, gold or other conductive material.

Similar to the embodiments described above, core conductor 360D is coated with a piezo-polymer layer 362. Sound pickup system 380D also comprises a surface electrode 364 disposed on the surface of piezo-polymer layer 362, and a thin external passivation layer 366 disposed on the outer surface of surface electrode 364. Surface electrode 364 and external layer 366 are again implemented as described above with reference to FIG. 3.

As shown in FIG. 6A, piezo-polymer layer 362, surface electrode 364 and external layer 366 each circumferentially surround core conductor 360B, or the previously applied layer, and extend the length of core conductor 360D. Similar to the embodiments described above with reference to FIGS. 4A-4E, a proximal end of core conductor 360D remains exposed to permit sound pickup system 380D to be connected to an additional component, such as an implant module.

As described above, a selected section of piezo-polymer layer 362 is polarized. In the embodiments of FIG. 3A, the distal region of piezo-polymer layer 362 is polarized and is referred to as polarized region 370. The remainder of piezo-polymer layer 362 remains unpolarized and is referred to as unpolarized region 372. When implanted in a recipient's cochlea, polarized region 370 detects pressure waves in the cochlea fluid, and generates electrical signals representative of the pressure waves. These electrical signals are relayed through core conductor 360D to the implant module. The section of sound pickup system 380D containing polarized region 370 is referred to herein as intracochlear acoustic sensor 350D, while the remainder of sound pickup system 380D is referred to as cable 352D.

The electrical signals generated by polarized region 370 of piezo-polymer layer 362 are relayed to implant module via inner signal electrode 676 of core conductor 360D. In certain embodiments, the relayed electrical signals are current signals that are converted to voltage signals by a charge amplifier (not shown) in the implant module. An exemplary charge amplifier is described below with reference to FIG. 8.

As would be appreciated, intracochlear acoustic sensor 350D is implanted through a natural or artificial opening in the recipient's cochlea. Intracochlear acoustic sensor 350D is also implanted so as to have minimal impact on the cochlear fluid dynamics. In certain embodiments, the natural or artificial opening through which sensor 350D is inserted should be sealed so as to reduce the impact on the fluid flow. Therefore, as noted above with reference to FIGS. 2A and 2B, in certain embodiments intracochlear sensor 350D and/or cable 352D may be configured to seal the opening through which sensor 350D is inserted. In alternative embodiments, a sealing member may be positioned on the surface of intracochlear sensor 350D or on the surface of cable 352D to seal the opening.

FIG. 6D is a partial cross-sectional view of one embodiment of a sound pickup system 380E in accordance with aspects of the present disclosure. As shown, sound pickup system 380E comprises intracochlear acoustic sensor 350E and cable 352E. Sound pickup system 380E also includes an elongate core conductor 360E. Core conductor 360E comprises an elongate porous core 680 formed from, for example, polyurethane. Disposed on the surface of porous core 680 is a thin metallic film 676. Metallic film 676 is sometimes referred to herein as inner signal electrode 676 and comprises a layer of, for example, platinum, titanium, gold or other conductive material.

Similar to the embodiments of FIG. 3, core conductor 360E is coated with a thin film piezo-polymer layer 362. Sound pickup system 380E also comprises a surface electrode 364 disposed on the surface of piezo-polymer layer 362, and a thin external passivation layer 366 disposed on the outer surface of surface electrode 364. Surface electrode 364 and external layer 366 are again implemented as described above with reference to FIG. 3.

As shown in FIG. 6D, piezo-polymer layer 362, surface electrode 364 and external layer 366 each circumferentially surround core conductor 360E, or the previously applied layer, and extend at least the length of core conductor 360E. In contrast to the embodiments described above, core conductor 360E does not extend through cable 352E. Rather, a wire 682 is connected to the proximal end of core conductor 360E. Wire 682 is embedded in a flexible coating 668 such as a flexible silicone rubber. Flexible coating 668 extends from the proximal end of piezo-polymer layer 362 to adjacent the proximal end of wire 682. The proximal end of wire 682 remains exposed for electrical connection with an implant module.

In the embodiments of FIG. 6D, flexible coating 668 is disposed about wire 682 so that the outer dimensions of flexible coating 668 are substantially the same as the outer dimensions of piezo-polymer layer 362, and surface electrode 364 is disposed on the outer surface thereof. Similarly, external layer 366 is disposed on the outer surface of surface electrode 364.

As shown in FIG. 6D, all or substantially all of piezo-polymer layer 362 is polarized so as to generate electrical signals representative of detected pressure waves. These electrical signals are relayed through core conductor 360E to wire 682 where they are provided to the implant module. The section of sound pickup system 380E containing polarized piezo-polymer layer 362 is referred to herein as intracochlear acoustic sensor 350E, while the remainder of sound pickup system 380E is referred to as cable 352E.

As noted above, cable 352E comprises wire 682 embedded in flexible coating 668. As shown, a section of wire 682 is formed into a helical shape and comprises a plurality of coils 674. Coils 674 provide strain relief to sound pickup system 380E. Specifically, coils 674 are embedded in flexible coating 668 to provide elongation of wire 682 if cable 352E is bent or otherwise subjected to external forces. This strain relief reduces the risk of the breakage of the electrical connection between an implant module and intracochlear sensor 350E in response to such flexing/bending of cable 352E.

As noted, the electrical signals generated by polarized piezo-polymer layer 362 are relayed to implant module via core conductor 360E and wire 682. In certain embodiments, the relayed electrical signals are current signals that are converted to voltage signals by a charge amplifier (not shown) in the implant module. An exemplary charge amplifier is described below with reference to FIG. 8.

In specific embodiments of the present disclosure, only intracochlear acoustic sensor 350E is implanted in the recipient's cochlea. In alternative embodiments, a portion of cable 352E is also implanted in the cochlea.

As would be appreciated, intracochlear acoustic sensor 350E is implanted through a natural or artificial opening in the recipient's cochlea. Intracochlear acoustic sensor 350E is also implanted so as to have minimal impact on the cochlear fluid dynamics. In certain embodiments, the natural or artificial opening through which sensor 350E is inserted should be sealed so as to reduce the impact on the fluid flow. Therefore, as noted above with reference to FIGS. 2A and 2B, in certain embodiments intracochlear sensor 350E and/or cable 352E may be configured to seal the opening through which sensor 350E is inserted. In alternative embodiments, a sealing member may be positioned on the surface of intracochlear sensor 350E or on the surface of cable 352E to seal the opening.

In the embodiments of FIG. 6D, the generally cylindrical structure of intracochlear sensor 350E has a slight curvature through its length so that the diameter at the mid-section 631 is smaller than that of the ends 632, 634. That is, intracochlear acoustic sensor 350E has a hourglass shape. In alternative embodiments, the intracochlear sensor 350E has a slight curvature through its length so that the diameter at the mid-section 631 is larger than that of the ends 632, 634.

Figure 7:
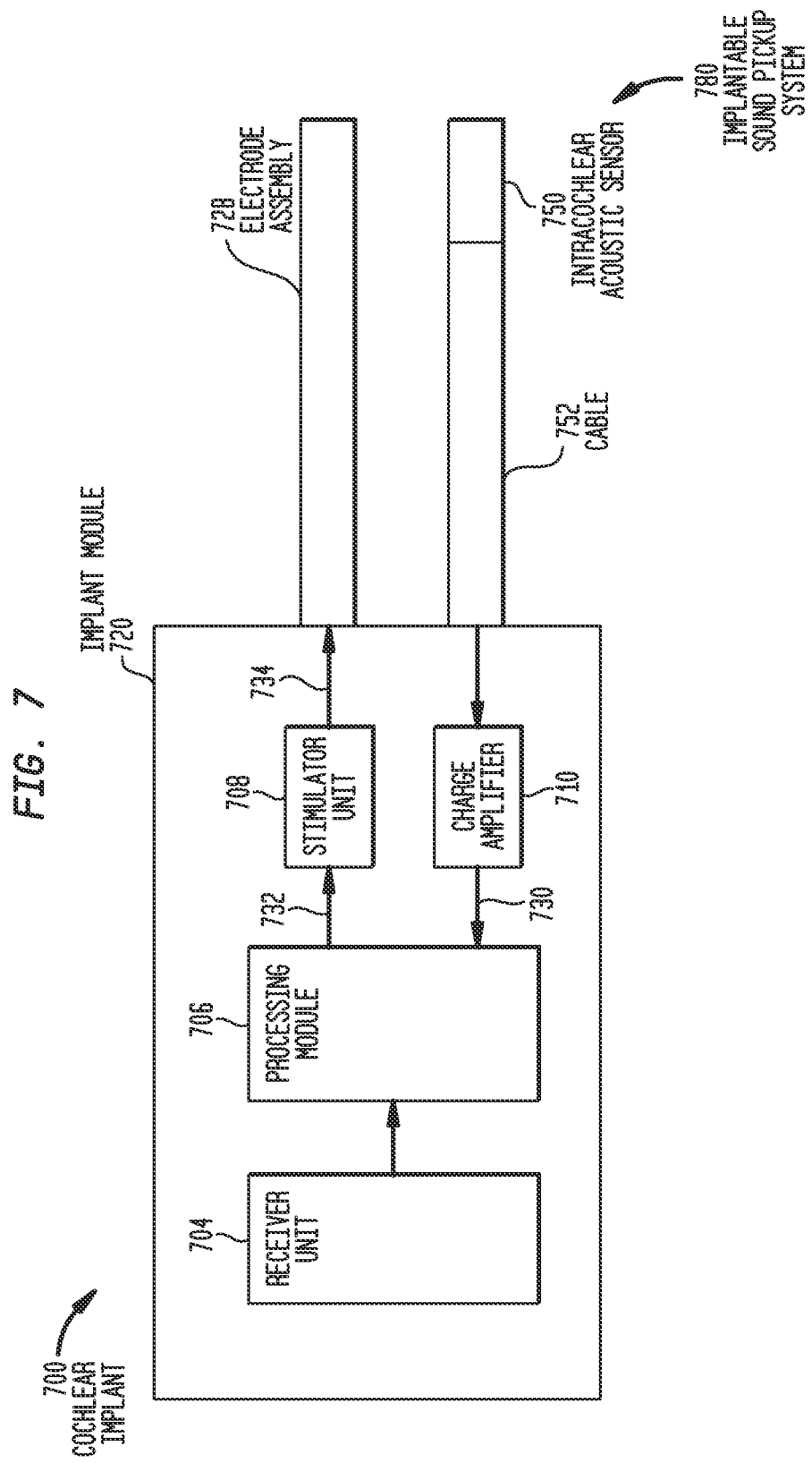
FIG. 7 is a functional block diagram of a totally implantable cochlear implant in accordance with embodiments of the present disclosure.

FIG. 7 is a functional block diagram of one embodiment of cochlear implant 100, referred to herein as cochlear implant 700. In the embodiments of FIG. 7, cochlear implant 700 is totally implantable; that is, all components of cochlear implant 700 are configured to be implanted under the skin/tissue of a recipient. Because all components of cochlear implant 700 are implantable, cochlear implant 700 operates, for at least a period of time, without the need of an external device.

As shown, cochlear implant 700 comprises a main implantable component, referred to as implant module 720. Implant module 720 includes a receiver unit 704, a processing module 706, a stimulator unit 708 and a charge amplifier 710. The embodiments of FIG. 7 are illustrative, and it would be appreciated that implant module may comprise one or more additional components. For example, it would be appreciated that implant module 720 may comprise an internal power source, such as a rechargeable battery, to provide power to the other components of cochlear implant 700.

As shown in FIG. 7, receiver unit 704 comprises an internal energy transfer assembly that receives power and/or data from an external device. In certain embodiments, receiver unit 704 may further be a transceiver unit that is configured to transmit data to an external device as well receive power and/or data from an external device.

As shown, cochlear implant 700 further comprises a sound pickup system 780 electrically connected to charge amplifier 710 in implant module 720. As described elsewhere herein, sound pickup system 780 comprises an intracochlear acoustic sensor 750, and a cable 752. As described in detail above, intracochlear acoustic sensor 750 is configured to sense a sound by detecting pressure waves with the recipient's cochlea fluid. Specifically, intracochlear acoustic sensor 750 converts detected pressure waves into an electrical signal that is related to charge amplifier 710 via cable 752. In the embodiments of FIG. 7, the proximal end of cable 752 is connected to charge amplifier via a feed through (not shown) extending through the exterior wall of implant module 720.

As explained below, charge amplifier 710 is configured to convert the electrical charge transferred along cable 752 from sensor 750 into an output voltage 730. This output voltage is provided to processing module 706. Using voltage output 730, processing module implements one or more speech processing and/or coding strategies to generate processed data signals 732 that are provided to a stimulator unit 708. Based on data signals 732, stimulator unit 708 generates electrical stimulation signals 734 for delivery to the cochlea of the recipient via electrodes (not shown) of electrode assembly 728. In the illustrative embodiment of FIG. 7, electrode assembly 728 is physically separate from sound pickup system 780. As described above, in an alternative embodiment electrode assembly 728 and sound pickup system 780 may be integrated into a single component.

Figure 8:
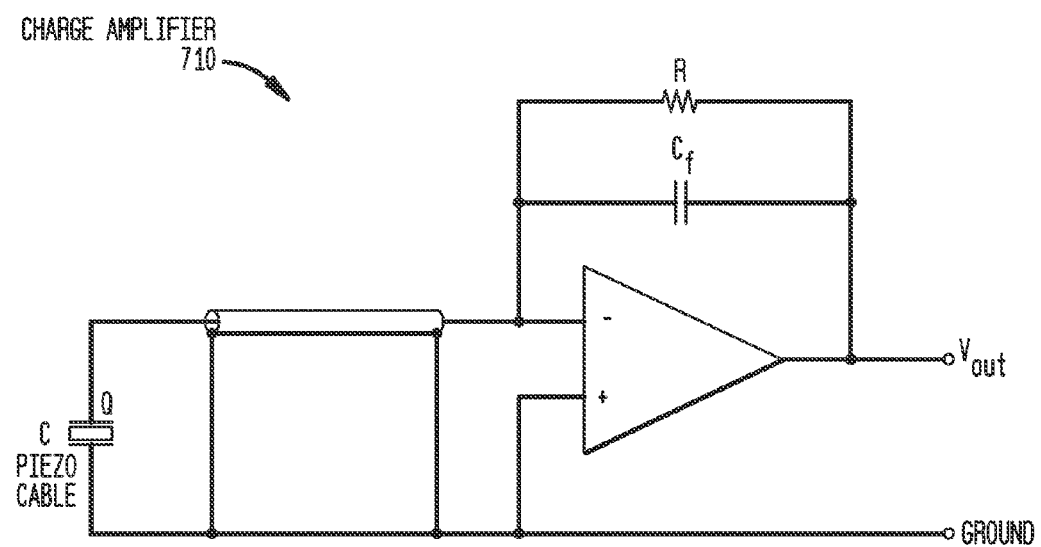
FIG. 8 is a schematic diagram of an exemplary charge amplifier in accordance with embodiments of the present disclosure.

FIG. 8 is a schematic diagram of one embodiment of charge amplifier 710 illustrated above in FIG. 7. As noted, charge amplifier 710 may be positioned within implant module 710 and is connected to intracochlear acoustic sensor 750 via a feed through and cable 752. More specifically, the electrical charge generated by the piezoelectric element of intracochlear acoustic sensor 750 is relayed through cable 752 to charge amplifier 710. Charge amplifier 710 converts this related electrical charge into a voltage output. In embodiments of the present disclosure, the voltage output by charge amplifier 710 is dependent only on its feedback capacitance and not on the source capacitance of intracochlear acoustic sensor 750. Therefore, by using the charge amplifier as the interface between intracochlear acoustic sensor 750 and the other electrical components of cochlear implant 700, all electronics may be positioned remotely from the acoustic sensor. As shown in FIG. 7, the components are hermetically sealed inside the implant module 720. This feature provides a sound pickup system 780 that is entirely completely passive and can be designed in the form of a shielded coaxial cable. In these embodiments of the present disclosure, cochlear implant 700 is referred to as operating in a charge mode.

Returning to the diagram of FIG. 8, C represents the source capacitance of the piezoelectric element of intracochlear acoustic sensor 750, while Q represents the electric charge present on the center core electrode (not shown). Furthermore, $C_f$ represents the feedback capacitance of charge amplifier 710. Therefore, $V_{out}$ is the output voltage and is determined by $V_{out}=Q/C_f$, which, as noted above, is independent of the source capacitance of the piezoelectric element within intracochlear acoustic sensor 750.

Figure 9:
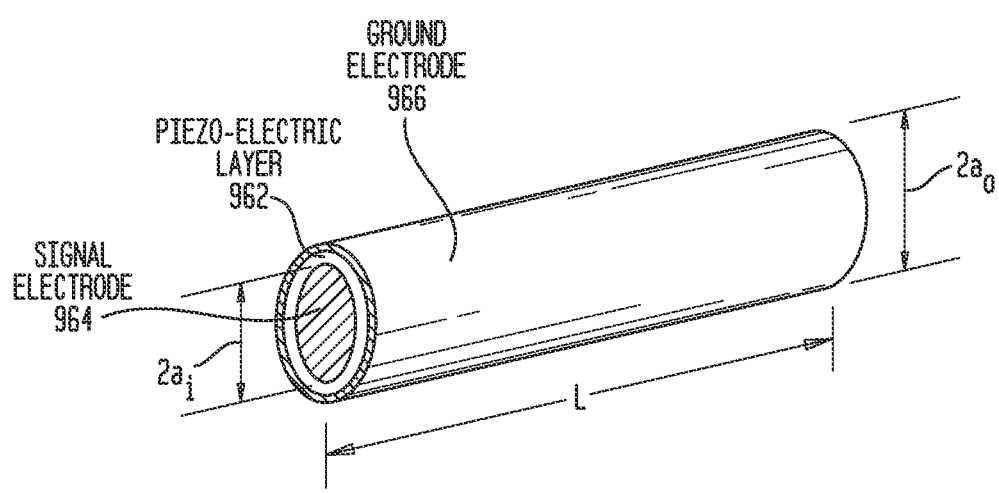
FIG. 9 is a schematic diagram illustrating the modeling of a piezoelectric element.

As noted above, embodiments of the present disclosure utilize a piezoelectric element to convert motion of the inner ear fluid into electrical charge. In specific embodiments, the piezoelectric element comprises a piezoelectric layer disposed about a core conductor. FIG. 9 illustrates theoretical aspects related to the design of a piezoelectric layer 962 that may be implemented in the embodiments described above. As noted, piezoelectric layer 962 has a cylindrical shape with a length L and a wall thickness t, and outer and inner radii of $a_o$ and $a_i$, respectively. Piezoelectric layer 962 is disposed about signal electrode 964 which is a solid conductor core bonded onto the inner surface of the tube. Ground electrode 966 is a metallic film coated on the outer surface of piezoelectric layer 962, which also serves as the EMI shielding. Each of electrodes 964, 966 are made of biocompatible metals such as Pt, Au, or other suitable materials. The EMI shielding of signal electrode 964 with ground electrode 966 may be beneficial given the presence of electrical stimulation current in the cochlea.

Under certain circumstances, the structure of an intracochlear acoustic sensor shown in FIG. 9 is similar to that of a coaxial cable. In such circumstances, the source capacitance of the intracochlear acoustic $C_s$ is given below by Equation (1) as:

$$C_s = \frac{2\pi\varepsilon L}{\ln\frac{a_o}{a_i}} \quad (1)$$

where $\varepsilon$ is the permittivity of PVDF material.

The intracochlear acoustic sensor of the FIG. 9 may be analyzed in a substantially similar manner as that previously used to analyze a small cylindrical hydrophone as reported by Langevin (1954) and Barger and Hunt (1964). See, Barger, J. E. and F. V. Hunt "Solid core probe hydrophone." J Acoust Soc Am 36(8): 1589-90 (1964); see also, Langevin, R. A. "The electro-acoustic sensitivity of Cylindrical Ceramic Tube." J. Acoust. So. Am 26: 421-7 (1954). The model, experimentally verified by Barger and Hunt by constructing and testing probe hydrophones made of PZT-5 ceramic cylinders with an outer diameter of $1/16^{th}$ inch and the radius ratio η of 0.68 is applied below.

Specifically, applying the above noted analysis, piezoelectric layer 962 is assumed to be polarized radially through its thickness. When hydrodynamic pressure $P_i$ is applied uniformly over the surface, two types of stresses are generated in piezoelectric layer 962 and in inner signal electrode 964. These stresses are described in the polar (r, θ) coordination system as the radial stress $\sigma_{rt}$ and $\sigma_{rc}$, and the tangential stress $\sigma_{\theta t}$ and $\sigma_{\theta c}$, respectively. Both the radial and tangential stress and displacement w can be expressed in Equations (2) below as:

$$\sigma_{rt} = Ar^{-2} + C, \ \sigma_{\theta t} = -Ar^{-2} + C, \text{ and } \sigma_{rc} = \sigma_{\theta c} = E(\text{const}) \quad (2)$$

$$w_{rt} = \frac{1}{Y_t}[-A(1+v_t)r^{-1} + C(1-v_t)r], \text{ and}$$

$$w_{rc} = \frac{1}{Y_c}E(1-v_c)r$$

where $Y_t$ and $Y_c$ are the Young's moduli; $v_t$ and $v_c$ are the Poisson's ratios of the tube and core, respectively. The A, C and E are the constants to be determined by boundary conditions. See, Timoshenko, S. and J. Goodier, *Theory of Elasticity*, (1951) New York, McGraw-Hill.

Since piezoelectric layer 962 is bonded to signal electrode 964, the continuity of the radial stress and displacement at the boundary between the inner surface of layer 962 and the outer surface of signal electrode 964 requires the following given in Equation (3) as:

$$\sigma_{rt}(r=a_0)=-P_i, \ \sigma_{rt}(r=a_i)=\sigma_{rc}, \text{ and}$$

$$w_{rt}(r=a_i)=w_{rc}(r=a_i) \quad (3)$$

where $\sigma_{rt}$ and $\sigma_{rc}$; $w_{rt}$ and $w_{rc}$ are the radial stress and displacement of piezoelectric layer 962 and signal electrode 964, respectively. By substituting Eq. (2) into (3), the radial and tangential stresses can be given by Equation (4) as:

$$\sigma_{rt} = \frac{-P_i}{1+\eta^2 G}[\eta^2 G a_o^2 r^{-2} + 1], \ \sigma_{\theta t} = \frac{-P_i}{1+\eta^2 G}[-\eta^2 G a_o^2 r^{-2} + 1] \quad (4)$$

where $\eta = a_i/a_o$, and $$G = \left[\frac{Y_c(1-V_t)}{Y_t(1-V_c)} - 1\right] \Big/ \left[\frac{Y_c(1+V_t)}{Y_t(1-V_c)} + 1\right] \quad (5)$$

Furthermore, the internal electrical field $e_r$ radially through the thickness of piezoelectric layer 962 is given by Equation (6) as:

$$e_r = g_{31}\sigma_{\theta t} + g_{33}\sigma_{rt} \quad (6)$$

Therefore, the open circuit voltage $V_o$ generated between the inner and outer electrodes is given by Equation (7) as:

$$V_o = \int_{a_o}^{a_i} e_r dr = \int_{a_o}^{a_i} [g_{31}\sigma_{\theta t} + g_{33}\sigma_{rt}] dr \quad (7)$$

By substituting Eq. (4) here, the open circuit voltage sensitivity of the Piezotube sensor can be found by Equation (8) as:

$$\frac{V_o}{P_i} = \frac{a_o(1-\eta)(1-\eta G)}{1+\eta^2 G}\left[g_{33}\frac{1+\eta G}{1-\eta G} + g_{31}\right] \quad (8)$$

In certain embodiments of the present disclosure, the outer diameter of an intracochlear acoustic sensor is less than 0.8 mm, which is approximately the same diameter as that basal region of certain conventional electrode assemblies. The intracochlear length of a sensor is dependent on, for example, the flexibility of the structure. In specific embodiments, it may be assumed that an implantable acoustic sensor is rigid, and that the intracochlear length is less than 8 mm.

Embodiments of the present disclosure have been primarily described with reference to using an intracochlear acoustic sensor as a primary sound pickup component. It would be appreciated that an intracochlear acoustic sensor of the present disclosure may also be used in as component of a system having other types of acoustic sensors. For example, the intracochlear acoustic sensor of the present disclosure may be used with one or more subcutaneous microphones, thereby enabling a choice of multiple types of acoustic inputs to be provided for a totally implantable cochlear implant system. Such an arrangement may improve the overall performance of the totally implantable cochlear implant system by providing a supplementary means of capturing sound, rather than having to rely on the performance of the particular subcutaneous microphone(s) used. The multiple sensor system can also facilitate the selective use of different types of sensors in various environmental conditions, where the users or the controlling software may select different settings for sensitivity, directivity and the like.

Further features and advantages of the present application may be found in commonly owned and co-pending U.S. patent application Ser. No. 10/986,812, filed Nov. 15, 2004, the content of which is hereby incorporated by reference herein. All documents, patents, journal articles and other materials cited in the present application are hereby incorporated by reference.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An intracochlear acoustic sensor implantable in a recipient's cochlea, comprising:
    a conductor; and
    a piezoelectric element disposed circumferentially about a length of the conductor and configured to detect pressure waves in the perilymph of the cochlea when the acoustic sensor is at least partially implanted in the cochlea, and to produce electrical signals corresponding to the detected pressure waves.

2. The intracochlear acoustic sensor of claim 1, further comprising:
    a surface electrode covering a length of the piezoelectric element; and
    an external passivation layer covering a length of the surface electrode.

3. The intracochlear acoustic sensor of claim 1, wherein the conductor comprises one or more metallic wires.

4. The intracochlear acoustic sensor of claim 1, wherein the piezoelectric element is a piezo-polymer.

5. The intracochlear acoustic sensor of claim 1, wherein the conductor comprises a non-conductive core having a metallic coating on a section of the surface thereof.

6. The intracochlear acoustic sensor of claim 1, wherein the conductor is a porous member.

7. The intracochlear acoustic sensor of claim 1, wherein a region of the piezoelectric element is polarized, and wherein a region of the piezoelectric element is unpolarized.

8. The intracochlear acoustic sensor of claim 1, wherein the piezoelectric element is a unitary layer disposed on a surface of the conductor.

9. The intracochlear acoustic sensor of claim 1, wherein the piezoelectric element is a polyvinylidene fluoride (PVDF) or PVDF copolymer film taped on the surface of, and spirally wound around the conductor.

10. An intracochlear implant comprising:
    an intracochlear acoustic sensor implantable in a recipient's cochlea, the sensor comprising:
        a conductor, and
        a piezoelectric layer disposed about a length of the conductor, wherein the piezoelectric layer is configured to detect pressure waves in a fluid of the cochlea when the acoustic sensor is at least partially implanted in the cochlea, and to produce electrical signals corresponding to the detected pressure waves.

11. The intracochlear implant of claim 10, wherein the conductor comprises one or more metallic wires.

12. The intracochlear implant of claim 10, further comprising:
    a surface electrode covering a length of the piezoelectric layer; and
    an external passivation layer covering a length of the surface electrode.

13. The intracochlear implant of claim 10, wherein the conductor comprises a non-conductive core having a metallic coating on a section of the surface thereof, and wherein the metallic coating extends the length of the non-conductive core.

14. The intracochlear implant of claim 10, wherein the conductor is a porous member.

15. The intracochlear implant of claim 10, wherein the piezoelectric layer is a piezo-polymer.

16. The intracochlear implant of claim 15, wherein the piezoelectric layer is a polyvinylidene fluoride (PVDF) or PVDF copolymer film taped on the surface of, and spirally wound around the core conductor.

17. The intracochlear implant of claim 10, wherein the piezoelectric layer is a unitary layer disposed on a surface of the conductor.

18. The intracochlear implant of claim 10, further comprising:
    an electrode assembly configured to deliver, to the recipient's cochlea, electrical stimulation signals generated based on at least the electrical signals produced by the piezoelectric layer.

19. The intracochlear implant of claim 18, wherein the electrode assembly and the intracochlear acoustic sensor form an integrated component.

20. The intracochlear implant of claim 10, wherein a region of the piezoelectric layer is polarized and wherein a region of the piezoelectric layer is unpolarized.

* * * * *